(12) United States Patent
Kana et al.

(10) Patent No.: US 9,913,732 B2
(45) Date of Patent: Mar. 13, 2018

(54) INTERBODY FUSION DEVICE WITH SEPARABLE RETENTION COMPONENT FOR LATERAL APPROACH AND ASSOCIATED METHODS

(71) Applicant: SpineSmith Partners, L.P., Austin, TX (US)

(72) Inventors: Richard J. Kana, Lexington, TX (US); Kevin Dunworth, Austin, TX (US); Ryan Medema, Pflugerville, TX (US)

(73) Assignee: SpineSmith Partners, L.P., Austin, TX (US)

( * ) Notice: Subject to any disclaimer, the term of this patent is extended or adjusted under 35 U.S.C. 154(b) by 0 days.

(21) Appl. No.: 13/668,037

(22) Filed: Nov. 2, 2012

(65) Prior Publication Data

US 2013/0297029 A1    Nov. 7, 2013

Related U.S. Application Data

(60) Provisional application No. 61/554,775, filed on Nov. 2, 2011.

(51) Int. Cl.
| | |
|---|---|
| *A61F 2/44* | (2006.01) |
| *A61F 2/30* | (2006.01) |
| *A61F 2/28* | (2006.01) |

(52) U.S. Cl.
CPC .......... *A61F 2/447* (2013.01); *A61F 2/30744* (2013.01); *A61F 2/4455* (2013.01); *A61F 2002/2817* (2013.01); *A61F 2002/2835* (2013.01); *A61F 2002/30131* (2013.01); *A61F 2002/30163* (2013.01); *A61F 2002/30266* (2013.01); *A61F 2002/30331* (2013.01); *A61F 2002/30471* (2013.01); *A61F 2002/30472* (2013.01); *A61F 2002/30484* (2013.01); *A61F 2002/30504* (2013.01); *A61F 2002/30556* (2013.01); *A61F 2002/30576* (2013.01); *A61F 2002/30579* (2013.01); *A61F 2002/30601* (2013.01); *A61F 2002/30607* (2013.01); *A61F 2002/30672* (2013.01); *A61F 2002/30787* (2013.01); *A61F 2002/30904* (2013.01); *A61F 2002/4415* (2013.01)

(58) Field of Classification Search
CPC .................. A61F 2/4455; A61F 2/4611; A61F 2002/4475; A61F 2/4465; A61F 2002/30133; A61F 2002/30387; A61F 2002/2835; A61F 2002/30131
USPC ...................... 606/246–249; 623/17.11–17.16
See application file for complete search history.

(56) References Cited

U.S. PATENT DOCUMENTS 6,461,359 B1 * 10/2002 Tribus et al. ................. 606/247
7,112,222 B2 * 9/2006 Fraser et al. ............... 623/17.11
(Continued)

*Primary Examiner* — Eduardo C Robert
*Assistant Examiner* — Tara R Carter
(74) *Attorney, Agent, or Firm* — Winstead PC

(57) ABSTRACT

The claimed invention is directed to a spinal fusion device comprising a load-bearing interbody component configured to fit between two adjacent vertebrae, wherein the interbody component comprises one or more openings to allow access to the vertebrae, a retention component that is configured to at least partially close the one or more openings of the interbody component and one or more fasteners that are coupled to the retention component to compress the two adjacent vertebrae to the interbody component, and methods of using a spinal fusion device.

5 Claims, 17 Drawing Sheets

(56) References Cited

U.S. PATENT DOCUMENTS

| | | | |
|---|---|---|---|
| 2002/0068977 A1* | 6/2002 | Jackson | A61F 2/4455 623/17.15 |
| 2005/0101960 A1* | 5/2005 | Fiere | A61B 17/7059 623/17.11 |
| 2005/0154459 A1* | 7/2005 | Wolek | A61F 2/44 623/17.11 |
| 2008/0021556 A1* | 1/2008 | Edie | A61F 2/44 623/17.11 |
| 2008/0243251 A1* | 10/2008 | Stad | A61F 2/442 623/17.16 |
| 2008/0269806 A1* | 10/2008 | Zhang et al. | 606/286 |
| 2009/0005870 A1* | 1/2009 | Hawkins | A61F 2/442 623/17.11 |
| 2009/0105830 A1* | 4/2009 | Jones et al. | 623/17.16 |
| 2009/0157187 A1* | 6/2009 | Richelsoph | A61F 2/4455 623/17.16 |
| 2011/0190892 A1* | 8/2011 | Kirschman | A61B 17/7059 606/247 |

* cited by examiner

INTERBODY FUSION DEVICE WITH SEPARABLE RETENTION COMPONENT FOR LATERAL APPROACH AND ASSOCIATED METHODS

CROSS-REFERENCES TO RELATED APPLICATIONS

This Application claims the benefit under 35 U.S.C. § 119(e) of U.S. Provisional Patent Application Ser. No. 61/554,775, filed Nov. 2, 2011, which is incorporated herein by reference in its entirety as if fully set forth herein.

FIELD OF THE INVENTION

This invention relates generally to the field of spinal fusion. In particular, this invention is drawn to spinal fusion devices and associated methods.

BACKGROUND OF THE INVENTION

The spine can be considered to be a series of movable segments made up of vertebrae and discs. Due to trauma, disease, and/or aging, the spine may be subject to degeneration. This degeneration may destabilize the spine and cause pain and/or nerve damage. Medical procedures are often required to either ease back pain, repair damage, or to prevent future damage.

One procedure that is often used to treat back pain or spinal damage is spinal fusion. Spinal fusion is a surgical technique used to combine two or more adjacent vertebrae. Supplemental bone tissue is used in conjunction with the patient's natural osteoblastic processes in a spinal fusion procedure. Spinal fusion is used primarily to eliminate back pain caused by the motion of the damaged vertebrae by immobilizing adjacent vertebrae. Conditions for which spinal fusion might be done include degenerative disc disease, treatment of a spinal tumor, a vertebral fracture, scoliosis, degeneration of the disc, spondylolisthesis, or any other condition that causes instability of the spine.

One problem with prior art spinal fusion techniques relates to device migration. For example, prior to complete bone fusion, a spinal fusion device may migrate from the desired position. In examples where bone screws are used, the insertion and tightening of the bone screws tends to cause device migration. Another problem with typical prior art spinal fusion techniques is that fusion devices, or associated plates or fasteners, protrude excessively from the spine, causing discomfort, damage, or danger to surrounding vascular or neurological tissues.

Another problem with prior art spinal fusion techniques relates to preparing the end plates of the vertebrae for fusion. Typically, a surgeon will scrape the end plates with surgical instruments (e.g., burrs, gouges, curettes, etc.), while holding adjacent end plates apart with another instrument. This procedure can be difficult and not exact. In addition, there is a danger of damaging nearby tissue while scraping the end plates.

Yet another problem with prior art spinal fusion techniques relates to the surgical approach, anatomic restrictions of the patient as a result of the surgical approach, instrumentation used to perform the fusion surgery, and the size and shape of the fusion device itself. In combination, these factors can result in large surgical wounds, massive disruption of, and danger to surrounding tissues during placement of the fusion device.

There is therefore a need for spinal fusion devices and instruments, as well as related spinal fusion procedures, that adequately treats degenerative disc disease and other spinal conditions, while providing improvements over the prior art.

SUMMARY OF THE INVENTION

An apparatus of the invention includes an intervertebral spinal fusion bearing device provided in any number of suitable sizes and shapes and is configured to fit between two adjacent vertebrae, the load-bearing, interbody fusion component having one or more openings to allow access to surgically prepare the end plates of the two adjacent vertebrae, a separate, interchangeable, stress-shielded retention component configured to at least partially close the one or more openings of the load-bearing fusion bearing component, preventing undesirable loss of fusion materials, and to prevent migration of the fully assembled interbody fusion device, using one or more fasteners coupled to the retention component to compress the two adjacent vertebrae to the load-bearing component.

In one embodiment is provided a spinal fusion device, including an open-sided, load-bearing, interbody fusion component configured to be collapsible to facilitate minimally invasive surgical techniques and easier insertion between two adjacent vertebrae, whereupon the collapsed load-bearing, interbody fusion component can be properly positioned, rotated, and expanded to its full size, wherein the load-bearing, interbody fusion component has an open end, to allow for subsequent endplate preparation and the in-situ application of fusion-enhancing material that will help to facilitate fusion between the endplates, and a separate, interchangeable, stress-shielded retention component configured to couple to the load-bearing, interbody fusion component, at least partially closing the open end to prevent loss or migration of the fusion-enhancing material from the load-bearing, interbody fusion component, wherein one or more fasteners are coupled to the retention component, having bores configure therethrough to allow at least one of the one or more fasteners to be inserted through the bores and making initial contact with a vertebral endplate, and/or ring apophysis, and/or an external wall, and/or edge of the vertebrae, to compress the two adjacent vertebrae to the fusion bearing component Another embodiment of the invention provides a method of fusing adjacent vertebrae including performing a lateral-approach discectomy, spreading the adjacent vertebrae, inserting a collapsed, open-sided, load-bearing interbody fusion component between the two adjacent vertebrae with an appropriate delivery instrument, rotating and positioning the device to engage the load-bearing edges of the fusion device with the endplates of the vertebrae, expanding the device to its fully opened size, preparing the end plates of the vertebrae for fusion by accessing the end plates through one or more openings formed in open-sided, load-bearing, interbody fusion component, placing a bone graft material between the endplates, completely filling the available space within the load-bearing interbody fusion component, then, securing a separate, interchangeable, stress-shielded retention component to the open-sided, load-bearing, interbody fusion component to prevent undesirable loss of fusion material, and one or more fasteners coupled to the retention component to compress the two adjacent vertebrae to the load-bearing, interbody fusion component to prevent migration of the assembled interbody fusion device, wherein the retention component includes bores configured to allow the one or more fasteners to be inserted through the bores and initiate contact with an endplate, and/or ring apophysis, and/or an external wall, and/or edge of the vertebrae, to compress the two adjacent vertebrae to the load-bearing component.

Yet another embodiment of the invention provides for a kit of fusion components to address various sizes and lordosis variations of a load-bearing interbody fusion component with interchangeable, mating retention components. For each embodiment of the open-sided, load-bearing, interbody fusion component associated with the invention, there is provided a series of mating plate sizes or retention components that would provide the appropriate matching anterior/posterior depth and superior/inferior dimensional height for varying sizes and lordosis of load-bearing, interbody fusion components to at least partially enclose the open side of the component Each retention component is provided with multiple bores therethrough, to allow at least one, but preferably two or more fasteners to be inserted through the bores and making initial contact with each adjacent vertebral endplate, and/or ring apophysis, and/or an external wall, and/or edge of the vertebrae, to facilitate compression of the two adjacent vertebrae to the load-bearing component. Said bores could be configured to allow for various degrees of fastener constraint, such as fully constrained, semi-constrained, or non-constrained, providing the surgeon with flexible options that may be needed to address variable intra-operative requirements or situations.

Still referring to the various embodiments of the retention component, the medial face (surface facing the open-sided load-bearing, interbody fusion component) has protrusions that provide alignment and/or attachment means for mating the retention component to the open-sided face of the load-bearing, interbody fusion component. Additionally, the mating medial face wall of the retention component would have a wall height that is less than the overall height of the corresponding mating surfaces of the open-sided load-bearing, interbody fusion component. In this manner, the mating surfaces, alignment features, and/or attachment means of the retention component (as well as the corresponding opposing features of the load-bearing component) would be shielded from any direct stresses that may be imparted on the entire assembled fusion device as a result of compressive loads exerted by the adjacent vertebral bodies. In particular, this difference in height should ensure that the vertebral compressive loads are more directly applied only to the load-bearing interbody fusion component.

In each embodiment of the retention component associated with the invention, there is an anti-backout mechanism used to prevent the bone fasteners from loosening and backing out of the vertebral bodies. As is described in detail below, the surgeon can turn the set screw with a driver, engaging a locking plate that rotates from a pre-set position to a final locked position. The protrusions of the locking plate will then be positioned over the ends of the fasteners, preventing them from backing out.

In another embodiment, this invention is an interbody fusion device that includes interlocking segments similar to a bicycle chain that is inserted into the intradiscal space. The segments follow the form of a previously inserted member. After the device has been inserted, the temporary inserted member is removed. The open portion of the so-formed device can be filled with bone graft material. A face plate (retention device) can then be applied which couples to the segmented implant, and fasteners used to secure the faceplate to the vertebral bodies.

In another embodiment, the interbody fusion device for lateral implantation between two vertebrae is includes a single monolithic generally U-shaped body (load bearing device) and a face plate (retention device).

In another embodiment, the interbody fusion device for lateral implantation between two vertebrae, including first and second upper and lower opposed, generally U-shaped members having channels for receipt of spacing members, spacing members configured to couple to the upper and lower members, and a face plate (retention device) adapted to couple to the upper and lower members and which includes bores for receiving fasteners that screw into the vertebrae to thereby secure the device in place between the vertebrae. The combination of the upper and lower members with the spacers creates a load bearing body.

The spinal intervertebral/interbody fusion implant of the present invention may be comprised of any suitable non-bone composition, including but not limited to polymer compositions (e.g. poly-ether-ether-ketone (PEEK) and/or poly-ether-ketone-ketone (PEKK)), ceramic, metal or any combination of these materials.

In addition, the spinal fusion implant of the present invention may be provided with any number of additional features for promoting fusion, such as apertures extending between the upper and lower vertebral bodies which allow a boney bridge to form through the spinal fusion implant of the present invention. Such fusion-promoting apertures may be dimensioned to receive any number of suitable osteoinductive agents, provided in various forms and configurations, including but not limited to allograft bone, bone marrow, Autologous Stem Cells, bone morphogenic protein (BMP) and bio-resorbable polymers, including but not limited to any of a variety of poly (D, L-lactide-co-glycolide) based polymers. The spinal fusion implant of the present invention preferably equipped with one or more lateral openings which may provide improved visualization at the time of implantation and at subsequent clinical evaluations.

The spinal fusion implant of the present invention may be provided with any number of suitable anti-migration features to prevent spinal fusion implant from migrating or moving from the disc space after implantation. Suitable antimigration features may include, but are not necessarily limited to, angled teeth formed along the upper and/or lower surfaces of the spinal fusion implant and/or spike elements disposed partially within and partially outside the upper and/or lower surfaces of the spinal fusion implant. Such anti-migration features provide the additional benefit of increasing the overall surface area between the spinal fusion implant of the present invention and the adjacent vertebrae, which promotes overall bone fusion rates.

The spinal fusion implant of the present invention may be provided with any number of features or radiographic markers for enhancing the visualization of the implant during and/or after implantation into a spinal target site. According to one aspect of the present invention, such visualization enhancement features may take the form of the spike elements used for anti-migration, which may be manufactured from any of a variety of suitable materials, including but not limited to a metal, ceramic, and/or polymer material, preferably having radiopaque characteristics. The spike elements may also take any of a variety of suitable shapes, including but not limited to a generally elongated element disposed within the implant such that the ends thereof extend generally perpendicularly from the upper and/or lower surfaces of the implant. The spike elements may each comprise a unitary element extending through upper and lower surfaces or, alternatively, each spike element may comprise a shorter element which only extends through a single surface (that is, does not extend through the entire height of the implant).

In any event, when the spike elements are provided having radiodense characteristics and the implant is manufactured from a radiolucent material (such as, by way of example only, PEEK and/or PEKK), the spike elements will be readily observable under X-ray or fluoroscopy such that a surgeon may track the progress of the implant during implantation and/or the placement of the implant after implantation.

The spinal fusion implant of the present invention is preferably intended for use with minimally invasive surgical techniques. More specifically, the implant is designed for an improved, minimally invasive, lateral surgical approach, meaning that the implant is inserted between adjacent vertebrae by being positionable from a lateral approach (left or right side) to extend from one lateral aspect to the other, but may be introduced in any of a variety of approaches, such as antero-lateral, postero-lateral, and transforaminal, without departing from the scope of the present invention (depending upon the sizing of the implant.

The assembled spinal fusion implant of the present invention may be provided in any number of suitable shapes and sizes depending upon the particular surgical procedure or need. The spinal fusion implant of the present invention may be dimensioned for use in the cervical and/or lumbar spine without departing from the scope of the present invention. For lumbar fusion, the spinal fusion implant of the present invention may be dimensioned, by way of example only, having a fully expanded anterior-posterior depth ranging between 15 and 35 mm, a height ranging between 8 and 20 mm, a medial-lateral length ranging between 25 and 60 mm, and a lordosis angle ($\Phi$) ranging between 0 and 20 degrees. For cervical fusion, the spinal fusion implant of the present invention may be dimensioned, by way of example only, having a medial-lateral width ranging between 11 and 20 mm, a height ranging between 5 and 12 mm, an anterior-posterior depth ranging between 10 mm and 17 mm, and a lordosis angle ranging between 0 and 8 degrees.

The spinal implant of the present invention may be introduced into a spinal target site through the use of any of a variety of suitable instruments designed for a minimally invasive surgical (MIS) approach, having the capability to releasably engage the spinal implant. In a preferred embodiment, the insertion instrument permits quick, direct, accurate placement of the collapsed spinal implant of the present invention into the cleared intervertebral space. According to one embodiment, the insertion instrument includes an engagement element dimensioned to positively engage into receiving apertures formed in the spinal fusion implant of the present invention and an elongate blade and/or fork member that supports the implant while it is rotated, positioned, and expanded within the disc space.

DETAILED DESCRIPTION OF EXEMPLARY EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related constraints, which will vary from one implementation to another. Moreover, it will be appreciated that such a development effort might be complex and time-consuming, but would nevertheless be a routine undertaking for those of ordinary skill in the art having the benefit of this. disclosure. The system to facilitate bone fusion and related methods disclosed herein boasts a variety of inventive features and components that warrant patent protection, both individually and in combination.

Figure 1:
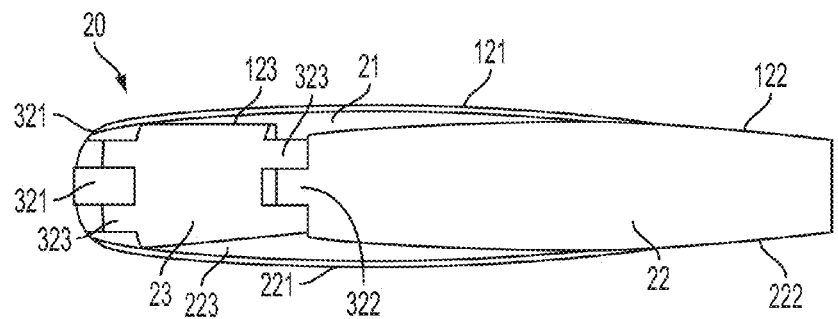
FIG. 1 is a cranial (superior) view, of the posterior aspect of a collapsed load-bearing fusion component, as it would look when being inserted between two adjacent vertebrae, showing a narrower posterior wall connected to a shorter, tapered lateral wall, laying on top of a wider anterior wall, which would create a 3-sided, lordodic lumbar component, wherein both the anterior and posterior walls having a representative medial- to-lateral cranial (superior) and caudal (inferior) radius of curvature.

FIG. 1, by way of example only, illustrates a posterior view of a 3-sided, collapsible-body, load-bearing component 20, in the collapsed state, having an anterior leg 21, a shorter lateral leg 23, and a posterior leg 22. The anterior, posterior and lateral legs may be provided with any number of features to; promote fusion, facilitate better matching of anatomic features of the spinal anatomy, or to simplify the lateral approach of a minimally invasive surgical (MIS) procedure. These may include convex medial/lateral and anterior-posterior cylindrical or spherical radii of curvature on the superior 121, 122 and inferior 221, 222 surfaces that are intended to more closely mate with the naturally occurring concave spherical radius of curvature found on the cranial and caudal surfaces of adjacent vertebrae. Similar or different offset radii of curvature may exist in the anterior/posterior direction versus the medial/lateral direction on the same surfaces 121, 122, 221, 222, creating a representative partial-sphere or elliptical effect on these surfaces. It should also be noted that the height of the anterior and posterior legs may be different.

In the preferred embodiment, the anterior leg height will be taller than the posterior leg height, which will impart the ability to replicate variable degrees of natural lordosis found in the lumbar spine. However, it is understood that all legs of the component could be the same height, thus imparting a device with Φ degrees of lordosis. Still referring to FIG. 1, the shorter lateral leg 23, may also have corresponding medial/lateral and offset anterior/posterior spherical radii of curvature on the proximal 123 and inferior 223 surfaces to more closely mate with the naturally occurring spherical radii of curvature found near the lateral aspect of the naturally occurring the cranial and caudal surfaces of the adjacent vertebrae. As can be seen in the representative figure, the amount of offset from centerline from the coronal plane, combined with the radius of curvature in the anterior/posterior direction of the lateral leg 23, will have a direct effect on the amount of lordosis the implant can replicate when it is expanded to its fully-opened state.

As further shown in FIG. 1, the three legs of the collapsible load-bearing fusion component are connected by a representative hinge mechanism. This hinge mechanism for this representative component is similar in configuration to a door hinge having a pin (not shown) between each leg and corresponding mating frame wings 321, 322, 323, on each leg.

Figure 2:
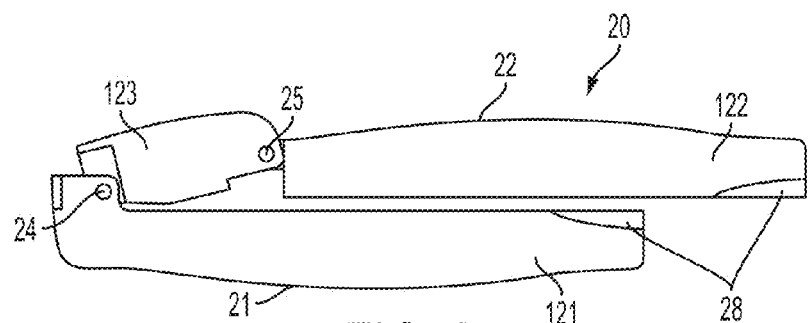
FIG. 2 shows an anterior view, of the superior aspect of a collapsed fusion bearing component.

Referring now to FIG. 2, an anterior view of the collapsed load-bearing fusion component 20 is shown, as it would appear for initial insertion, between two adjacent vertebrae. The preferred orientation for insertion would provide for the anterior leg to be placed in an inferior orientation (large surface down), leading with the closed end of the collapsed device, into the wound and between the adjacent vertebrae, into the cleared disc space. The approximate locations of the previously described hinge pins 24, 25, can now be seen on the superior surfaces of the anterior and lateral legs 121, 123. It should be understood that the hinge mechanism described herein is merely representative of any type of hinge mechanism that would allow the component to collapse in order to obtain a lower profile for insertion.

As further shown in FIG. 2, there can be seen clearance cuts 28, near the open ends of both the anterior 21 and posterior 22 legs at the juncture of the interior walls and superior surfaces 121, 122. The clearance cuts provide additional room for fastening mechanisms, such as bone screws, to be placed as widely as possible relative to the boundaries of the spinal fusion device, in order to provide the best opportunity for access to the strongest, most dense bone found near the anterior and posterior cortical aspects of the vertebral bodies.

Figure 3:
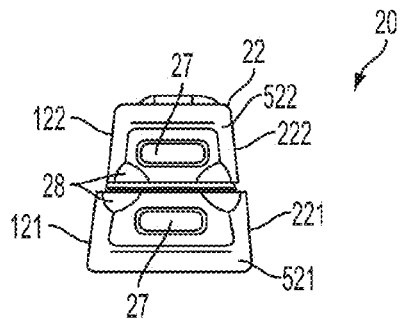
FIG. 3 is a lateral end view of a collapsed fusion bearing component, showing the connection features for a retention component that would cover the open-side of the fusion bearing component and clearances for bone attachment means, such as screws, as seen when being inserted from a lateral approach.
Figure 4:
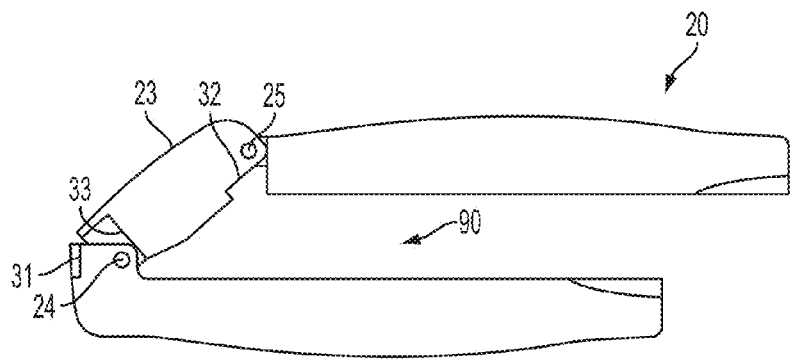
FIG. 4 shows a superior or proximal view of the load-bearing fusion component in a partially expanded or partially un-collapsed configuration, after insertion and 90 degree rotation posteriorly. The approximate location and function of hinge features can be seen.
Figure 5:
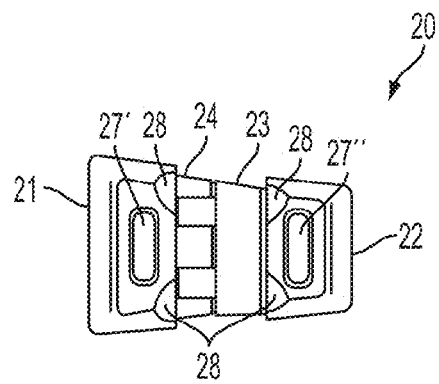
FIG. 5 is a lateral end view of the load-bearing fusion component in a partially expanded or un-collapsed configuration, as seen from a lateral approach, after the implant has been rotated posteriorly; showing the connection features for a retention component that would cover the open-side of the load-bearing fusion component and clearances for bone attachment means, such as screws, with a partial view of the opposing lateral (closed) side of the hinged load-bearing fusion component.

FIG. 3 depicts the lateral view of the collapsed load-bearing fusion component 20, shown in FIG. 2. Some common attributes are shared among the various embodiments. More specifically, the clearance cuts 28, near the open ends of both the anterior 21 and posterior 22 legs can be seen at the juncture of the interior walls and both the superior surfaces 121, 122 and the inferior surfaces 221, 222. Additionally, connection features 27', 27" are shown in the ends 521, 522 of the anterior and posterior legs 21, 22. The connection features of the preferred embodiment provide may serve multiple functions. First, the connection feature provides a means to align and attach insertion and distraction instrumentation to the fusion bearing component. Second, they provide a similar function once the fusion bearing component is appropriately placed and all fusion preparation steps have been completed, by providing a mating feature for the separate retention component FIGS. 4-5 depict superior and lateral views, respectively, of the load-bearing fusion component 20, following insertion between the vertebral bodies and 90 degree rotation (posteriorly) of the entire component (in the coronal plane) to position the component for expansion. More specifically, FIG. 4 illustrates the action of the hinge mechanism as the implant is partially expanded. As expansion of the component occurs, the closed lateral (side) leg of the component 23, pivots laterally around the anterior pivot pin 24. Simultaneously the posterior leg of the component pivots about the posterior pivot pin 25. As the lateral and posterior legs slide synchronously in the lateral direction, the component begins to form a U-shaped box-like shape creating a hollow space 90, between the three legs of the component. The pivot rotation would ultimately stop when the lateral and posterior legs, pivoted approximately 90 degrees around the pivot pins 24, 25 and engaged the pivot stops 31, 32, 33, located in the ends of the anterior and lateral legs.

FIG. 5 depicts the lateral view of the load-bearing fusion component at the same point of partial expansion described by FIG. 4. Utilizing an insertion and/or expansion instrument attached to the connection features 27', 27", the anterior leg would be held stationary between the vertebrae by fixing its location with at the connection feature 27', while the posterior and lateral legs 22, 23 are pushed laterally at point 27". It is envisioned that additional features on the instrumentation would locate and stabilize the load-bearing device at various locations around the anterior and posterior walls of the anterior and posterior legs of the component. One such location could be the clearance cuts 28 located at the superior and inferior intersection of the internal walls at the open lateral ends of the anterior and posterior legs 21, 22.

Figure 6:
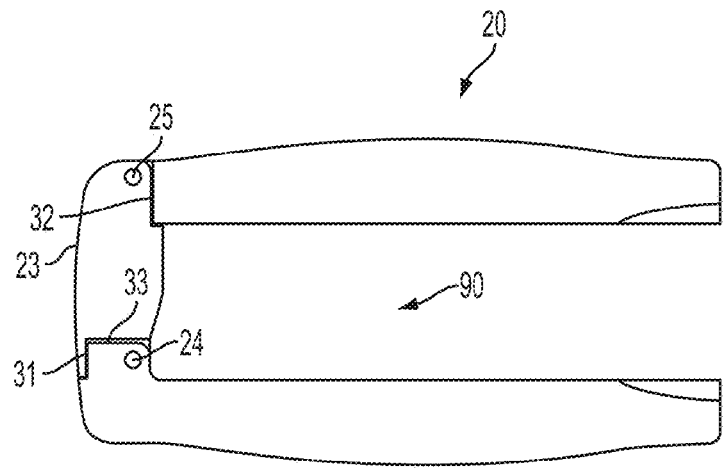
FIG. 6 is a superior view of the load-bearing fusion component in a fully expanded configuration, with the hinge features and built-in stop features fully engaged.
Figure 7:
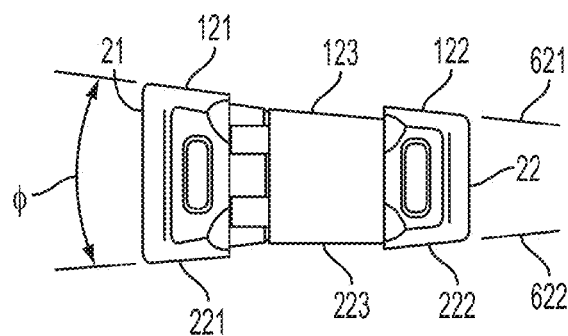
FIG. 7 is a lateral end view of the load-bearing fusion component in a fully expanded configuration, as seen from a lateral approach, after the implant has been rotated posteriorly; showing the connection features for a retention component that would cover the open-side of the load-bearing fusion component and clearances for bone attachment means, such as screws, with a full view of the opposing lateral (closed) side, and the anterior-lateral hinge of the load-bearing fusion component.

FIGS. 6 and 7 are sequential views of FIGS. 4 and 5, depicting superior and lateral views of the load-bearing fusion component 20, following complete expansion of the component. As can be seen in FIG. 6, the lateral leg 23 has fully engaged the pivot stops 31, 33 and completed its rotation around pivot pin 24. In addition the posterior leg has completed its rotation about pivot pin 25, and fully engaged the pivot stop 32, resulting in the fully-formed and expanded load-bearing fusion component.

Referring now to FIG. 7, it is apparent that the preferred embodiment of the fully formed load-bearing fusion component provides a lordodic (angle Φ) component to its geometry which is a resultant of the differences in height between components 21 & 22, as defined angle created between the superior plane 621, (drawn across the superior surface 121 of the anterior leg 21 to the superior surface 122 of the posterior leg 22) and the corresponding inferior plane 622, (drawn across the inferior surface 221 of the anterior leg 21 to the inferior surface 222 of the posterior leg 22). Ideally, the vertical height between planes 621 and 622 will always be slightly greater than the height of the mating planer surfaces 41 and 43 of the retention component 40, as shown in FIG. 13-C. This dimensional difference would assure that the compressive loads generated by the vertebral bodies, would always be applied to the load-bearing fusion component and not on the retention component. Additionally, one skilled in the art would recognize that surfaces 121, 123, and 122 could be configured to mate together in a radial convex arc in order to match the natural concavity of the caudal endplate of the adjacent vertebral body. Similarly, surfaces 221, 223, and 222 could also be configured to mate together in a radial convex arc in order to match the natural concavity of the cranial endplate of the adjacent vertebral body.

Figure 8:
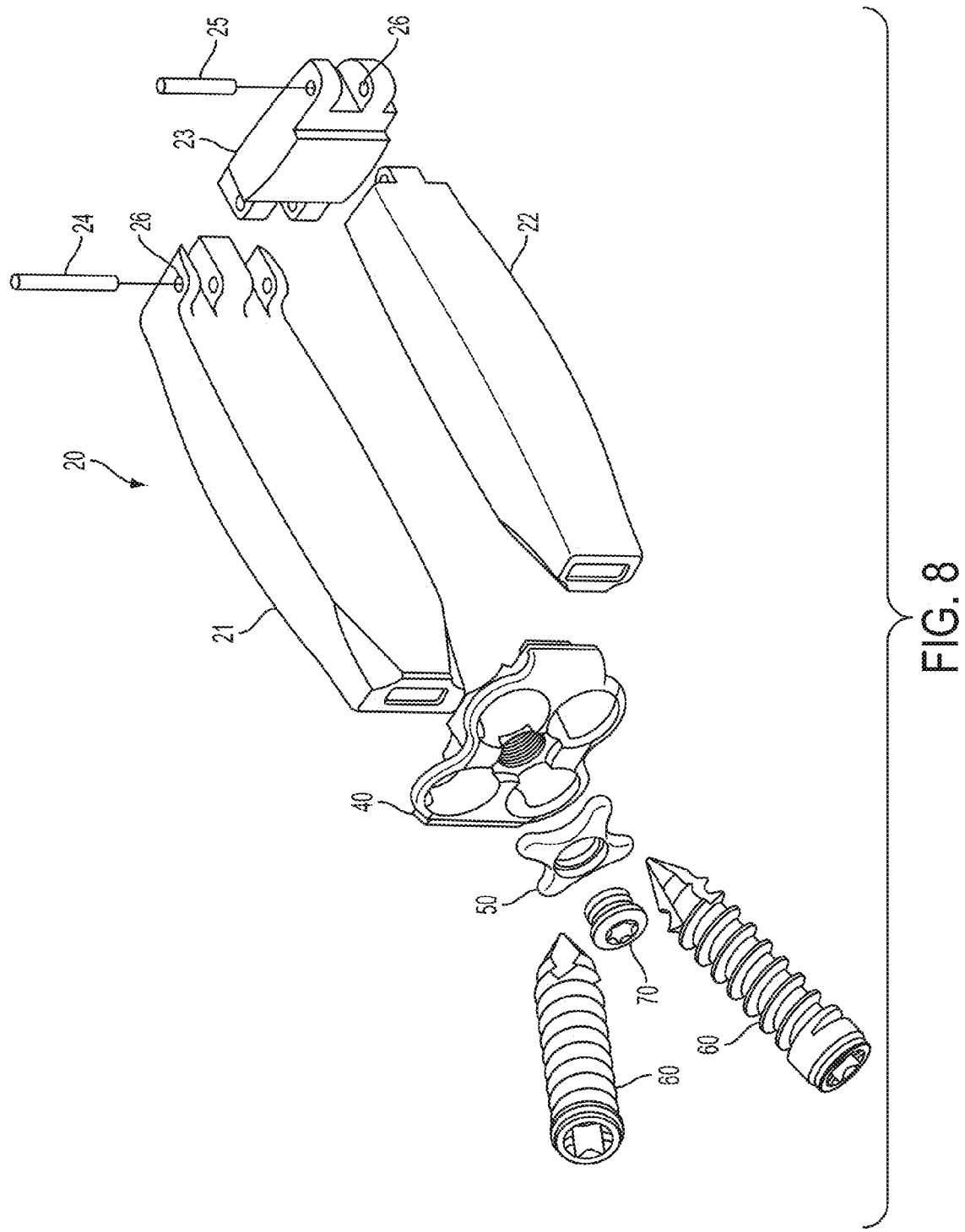
FIG. 8 is an exploded isometric view of the load-bearing fusion component, the separable retention component, the anti-backout mechanism, the locking or set screw, and bone screw fasteners.
Figure 9:
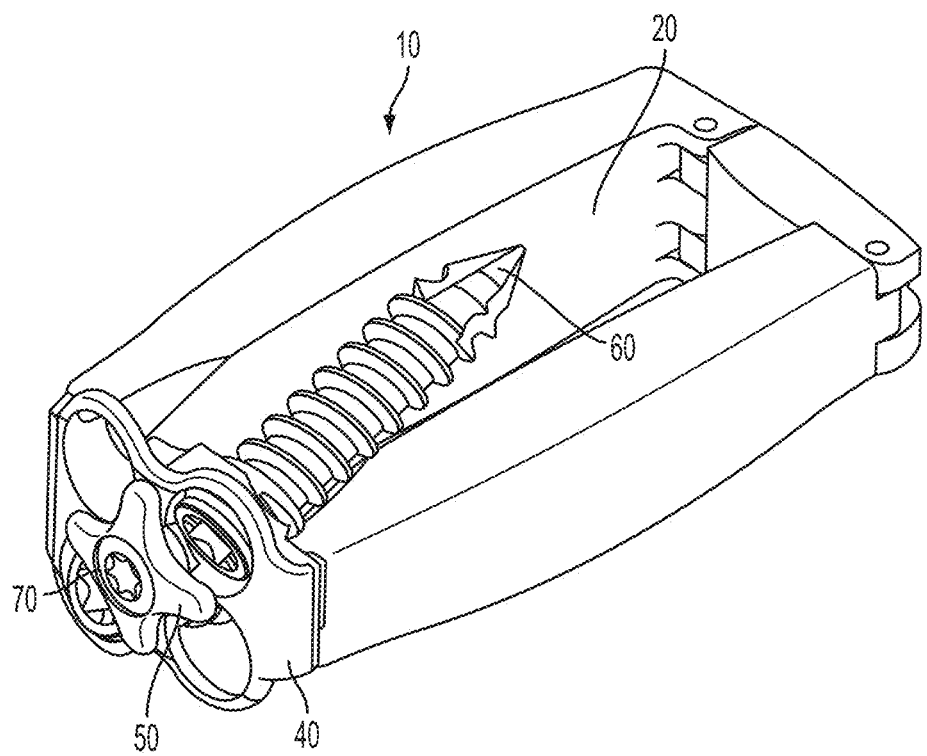
FIG. 9 is an assembled isometric view of the entire intervertebral spinal fusion bearing device, including the load-bearing fusion component, the separable asymmetric retention component, the anti-backout mechanism (in the pre-set position—not engaged), the locking or set screw, and bone screw fasteners.

FIGS. 8 and 9 are representative embodiments of an exploded and assembled isometric view of the entire intervertebral spinal fusion device 10 comprised of the load-bearing fusion component 20, composed of; the anterior, lateral and posterior legs 21, 23 and 22, the hinge pins 24, 25, inserted in pivot points 26, the separable retention component 40, the anti-backout mechanism 50, the locking or set screw 70, and bone screw fasteners 60.

Figure 10:
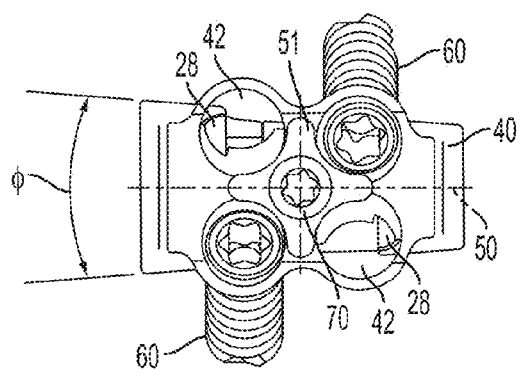
FIG. 10 is an assembled lateral view of the load-bearing fusion component, the retention component, the anti-backout mechanism (in the pre-set position - not engaged over the heads of the bone screw fasteners), the locking/set screw, and bone screw fasteners.
Figure 11:
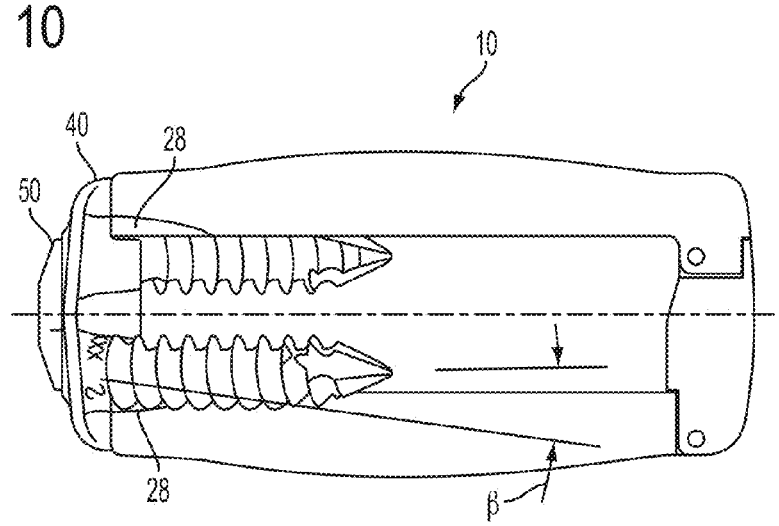
FIG. 11 is superior view the entire intervertebral spinal fusion bearing device in a fully expanded configuration, with the retention component, the anti-backout mechanism (in the pre-set position—not engaged), and bone screw fasteners.
Figure 12:
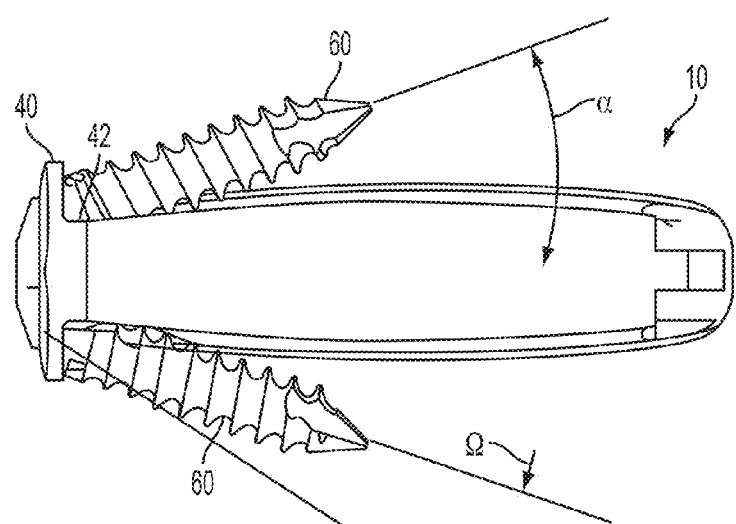
FIG. 12 is a posterior view the entire intervertebral spinal fusion bearing device, in a fully expanded configuration, having a representative medial-to-lateral cranial and caudal radius of curvature, with the retention component, the anti-backout mechanism (in the pre-set position—not engaged), and bone screw fasteners.

FIGS. 10-12 depict lateral, superior and posterior views, respectively, of the preferred embodiment of the entire intervertebral spinal fusion device 10. In particular, FIG. 10 illustrates the asymmetric shape of the retention component 40, when viewed laterally, having a lordodic profile (angle Φ) to match the lordosis of the mating load-bearing fusion component. Further, FIG. 10 illustrates one of many potential relative positions of the divergent bone screws fasteners 60, inserted through bores 42 of the retention component. Clearance cuts 28 are also visible on the open-end lateral side of the load-bearing component, through the bores of the retention component. One skilled in the art would appreciate that the relative differences between the bore sizes, bore angle, and fastener sizes, coupled with the presence of the clearance cuts in the load-bearing component, creates variable degrees of constraint, and can dictate the amount of angulation that could be exerted on the fasteners during placement in the vertebral bodies.

Still referring to FIG. 10, the anti-backout mechanism 50 and locking set screw 70 are shown, in the pre-deployed position. When deployed by twisting the locking set screw, a locking wing 51 on the anti-backout mechanism would rotate over each head of the bone screw fasteners, preventing migration of the fastener(s).

FIG. 11 is a cranial (superior) view of the preferred embodiment of the entire intervertebral spinal fusion device 10. In particular, FIG. 11 illustrates the additional potential variable (anterior-posterior) angulation (angle β) that could be achieved as a result of the presence and size of the clearance cut(s) in the anterior and posterior legs.

FIG. 12 is a posterior view of the preferred embodiment of the entire intervertebral spinal fusion device 10. In particular, FIG. 12 illustrates the range of additional angulation, beyond the minimum desired penetration angle, which could be achieved depending on differences in the designed constraint between the bore sizes and the fastener sizes. The minimum penetration angle α, is that angle which assures the surgeon that the fastener will always penetrate the boney endplate of the vertebral body, and not skive off the surface, into the disc space between the vertebral bodies. The maximum penetration angle (angle Ω), is the angle which can be achieved as a result of the amount of constraint (or lack of constraint) between the inner diameter of the bore 42 and the capture diameter of the fastener 60.

Figure 13A:
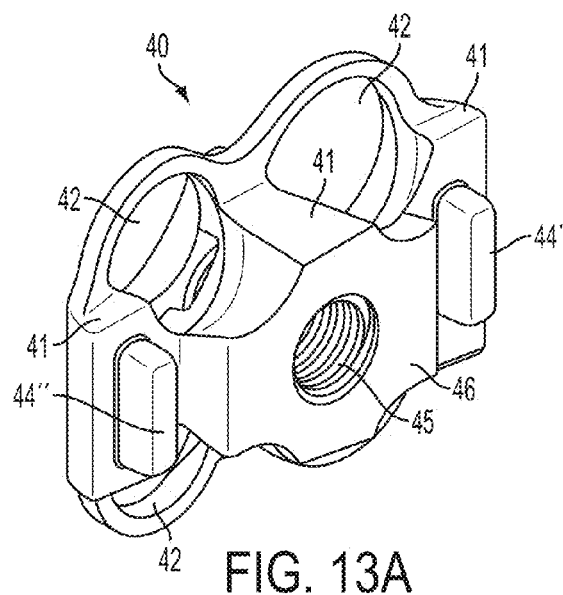
FIGS. 13A-13C illustrate isometric, posterior-to-anterior, and lateral views respectively, of the retention component.
Figure 13B:
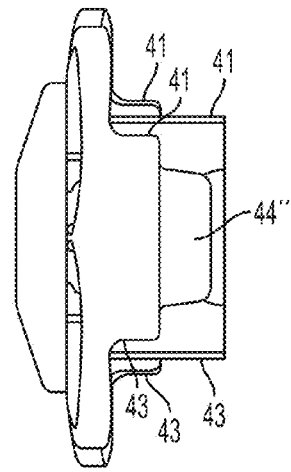
Figure 13C:
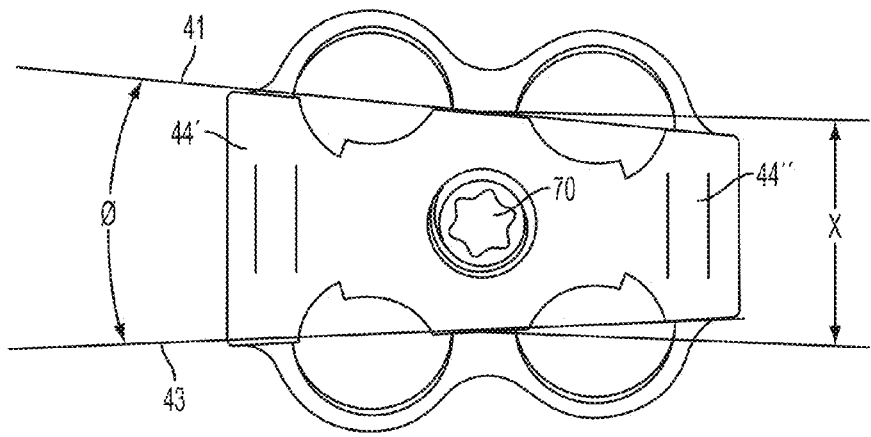

FIGS. 13A-13C depict isometric, posterior-to-anterior, and lateral views respectively, of the retention component. As shown in FIG. 13-A, illustrating one exemplary embodiment, the retention component has alignment features 44', 44" that would mate with corresponding alignment features 27', 27" of the load-bearing component 20. It is understood that these alignment features could be either protrusions or indentions in nature on either component, or a combination of protrusions and indentions on both components. It should also be noted that the alignment components could also be configured to have attachment means (not shown), incorporated as part of this feature. Also shown, is the superior lordodic planar surface 41, which would ideally sit below the planar surface 621 on the load-bearing component, as seen in FIG. 7. Through-bore 45, projecting through boss feature 46, is threaded to accommodate the locking set screw 70. Alternatively, this bore could be utilized in-situ, after attachment of the retention component, for the delivery of osteoinductive factors, such as BMP or stem cells, to the center of the device, before applying the anti-backout mechanism and locking set screw. The boss feature 46 is configured to act as a secondary alignment feature, mating with the interior walls of the anterior and posterior legs of the load-bearing component. A secondary benefit of this feature is to capture and compress the graft material, preventing unintentional migration of said materials after they are placed in the hollow center of the expanded load-bearing component.

Still referring to FIG. 13-A, this embodiment illustrates bores 42 for the placement of fasteners, such as bone screws, which would be utilized to secure the retention component, to the adjacent vertebral bodies, thus preventing the spinal fusion assembly, as a whole, from migrating post-operatively.

FIG. 13-B is a posterior edge view of the retention device. FIG. 13-C is a lateral end view of the retention component, illustrating the mating planar surfaces 41 and 43, and the lordotic angle Φ that they create to match the lordodic angle of the mating load-bearing component. Ideally the relative difference in vertical height between planes 41 and 43, measured anywhere along these surfaces would be less than the corresponding relative difference in vertical height between planes 621 and 622 of the load bearing component, when measured in the same location. This difference in height would be necessary in order to assure that the compressive loads generated by the vertebral bodies, would always be applied to the load-bearing fusion component, and not on the retention component, its alignment features or any incorporated capture means.

Figure 14A:
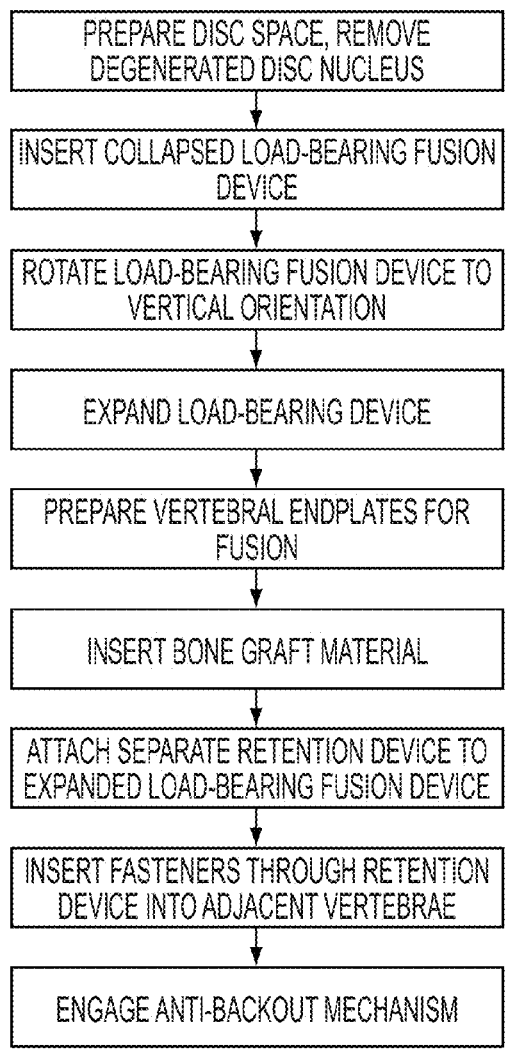
FIG. 14A is a flow diagram describing the basic steps associated with the method for implantation of this invention.
Figure 14B:
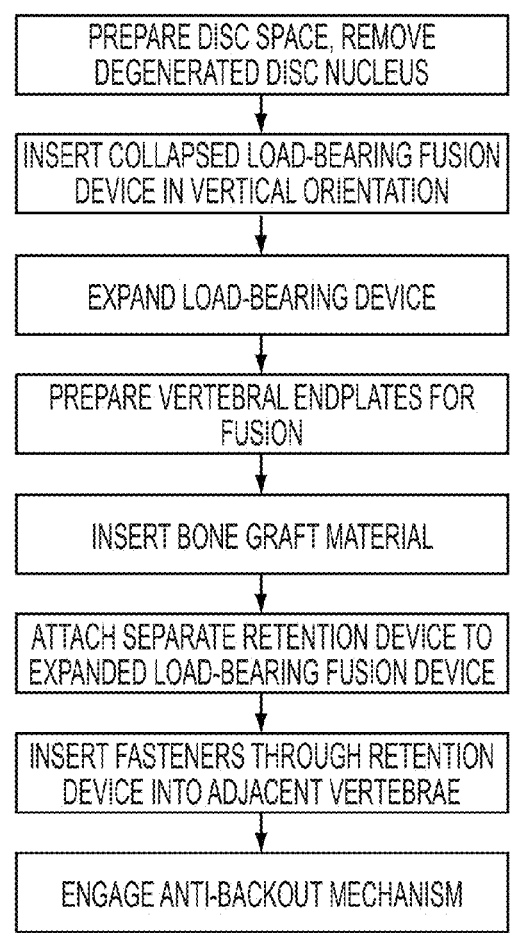
FIG. 14B is a flow diagram describing the basic steps associated with an alternate method for implantation of this invention, describing the method of implantation by insertion of the device in a vertical orientation, not requiring the need for the rotation step, described in FIG. 14A.

FIG. 14A is a flow diagram describing the basic steps associated with one method for implantation of this invention. FIG. 14B is a flow diagram describing the basic steps associated with an alternate method for implantation of this invention, not requiring in-situ rotation of the device following insertion of the invention between the vertebrae.

In order to use the system of the illustrative embodiment to perform a spinal fusion procedure as described in FIGS. 14A and 14B, the clinician must first prepare the disc space by performing a lateral-approach discectomy and spreading the adjacent vertebrae with an appropriate spreading instrument/device. A clinician can utilize the system in either an open or minimally invasive spinal fusion procedure. In either type of procedure, a working channel is created in a patient that reaches the targeted spinal level. After the creation of that channel, the discectomy may be performed via any number of well known preparation tools, including but not limited to cobbs, kerrisons, rongeurs, pituitaries and curettes. The prepared disc space is then assessed by the clinician for sizing of the load-bearing interbody fusion component.

After the appropriately sized load-bearing interbody fusion component is chosen, it is attached in its collapsed configuration onto the appropriate delivery instrument, inserted through the working delivery channel and into the prepared discectomy space between the two adjacent vertebrae. Utilizing the delivery instrument, the implant is then rotated and positioned to engage the load-bearing edges of the fusion device with the endplates of the vertebrae. The clinician would then utilise the delivery device to expand the load-bearing device to its fully opened size. At this point the clinician would typically confirm proper placement with intra-operative x-ray or fluoroscopy images. If needed, adjustments to the position of the device would be made at this time. If satisfied with the placement, the delivery device would be released from the implant and removed from the working channel, along with the vertebral body spreader device. The clinician would then proceed with preparing the end plates of the vertebrae for fusion by accessing the end plates through the open end of the open-sided, load-bearing, interbody fusion component. This may be performed via any number of well known preparation tools, including but not limited to curettes and rasps in order to create a good, bleeding bone bed. An appropriate bone grafting material would then be inserted to completely fill the available space within the load-bearing interbody fusion component and between the endplates.

Following graft placement, the clinician would secure a separate, interchangeable, stress-shielded retention component using the appropriate delivery instrument, to the open-sided, load-bearing, interbody fusion component to prevent undesirable loss of fusion material. Once satisfied with placement, one or more fasteners would be inserted through to the retention component into the adjacent vertebrae to compress the two adjacent vertebrae to the load-bearing, interbody fusion component thus preventing migration of the assembled interbody fusion device. The design variations of the retention component include bores configured to allow the one or more fasteners to be inserted through the bores and initiate contact at various angles, with an endplate, and/or ring apophysis, and/or an external wall, and/or edge of the vertebrae to compress the two adjacent vertebrae to the load-bearing component.

Once the fasteners are in place, the clinician would then engage an anti-backout mechanism to secure the fasteners and prevent undesired migration of the fasteners.

The exemplary collapsible interbody fusion device system is provided as a kit composed of multiple heights, widths, lengths and lordosis angles of load-bearing interbody fusion components, various sizes of retention devices to match the heights, widths, and lordosis angles of load-bearing interbody fusion components and screws of various lengths, thread pitch, and diameters to accommodate the anticipated vertebral body sizes and bone quality of vertebral bodies often found during fusion surgery.

Figure 15:
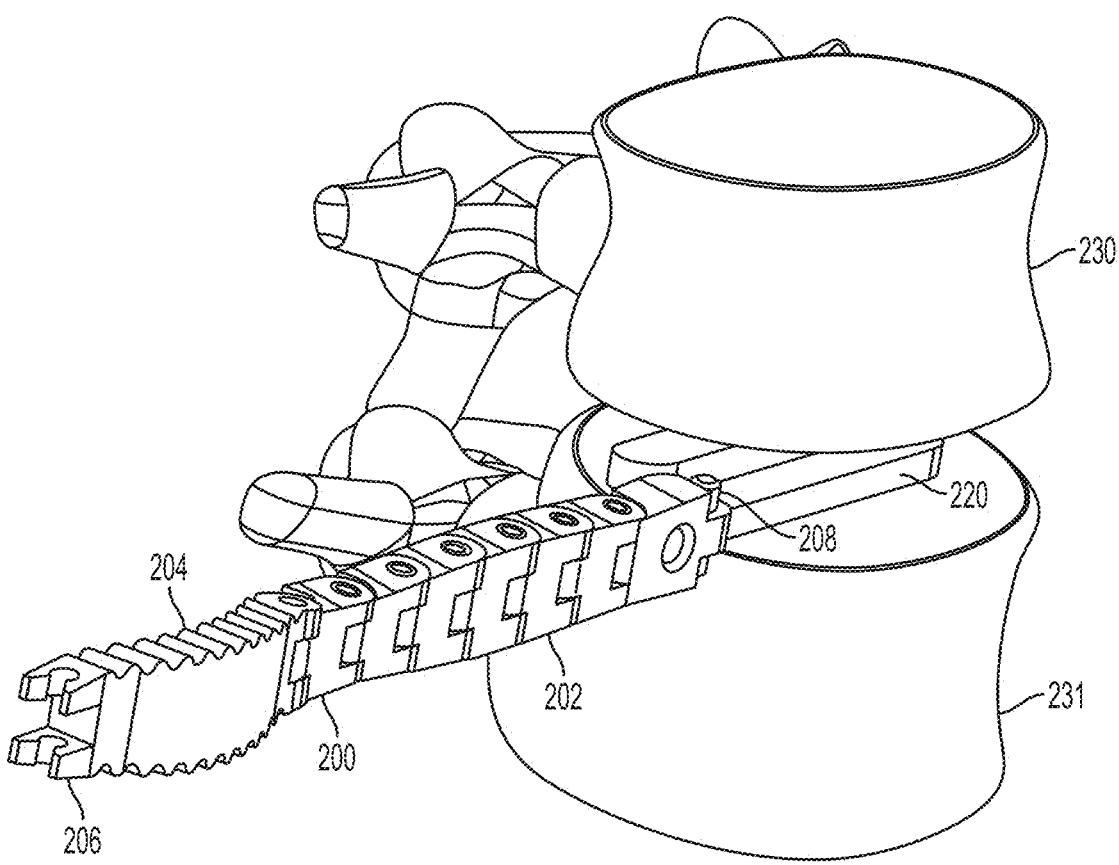
FIGS. 15-17 illustrate another embodiment of this invention that employs a chain-like, segmented portion configured to bend and straighten to thereby form a generally U-shaped component.
Figure 16:
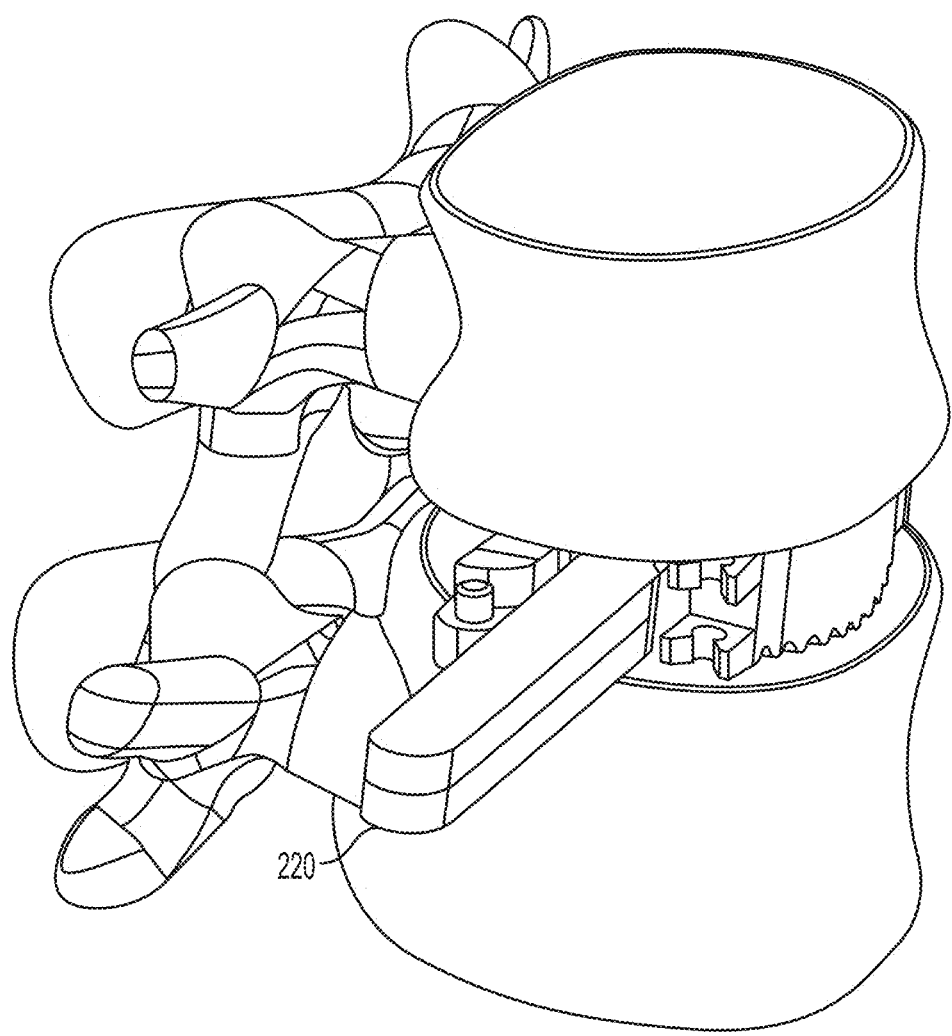
Figure 17:
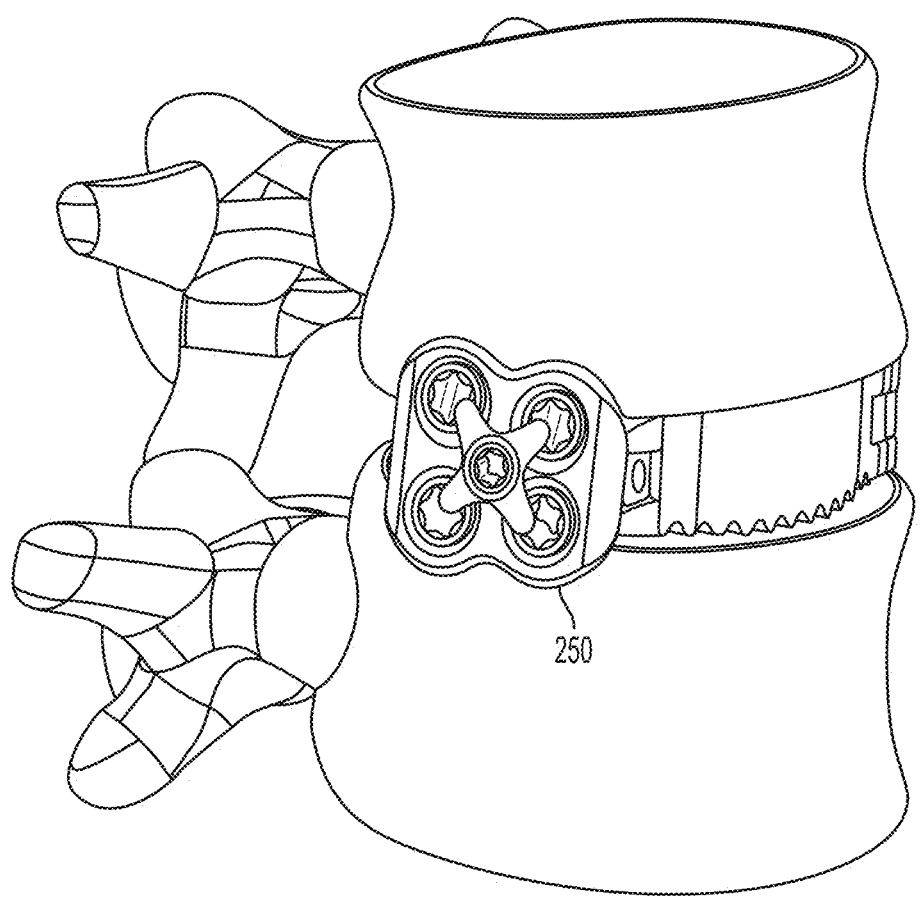

FIGS. 15-17 show another embodiment of the invention. In this embodiment, the device includes a partially segmented member 200 which includes links that are configured to be capable of following the guide members 220 to thus turn and form a generally U-shaped body that sits between the vertebrae 230, 231. The partially segmented member 220 includes articulated segments 202 that connect to anterior piece 204 which forms one side of the device. The segments 202 include a coupler 208 for engagement with a faceplate 250 that includes a locking mechanism. Likewise, the anterior piece 204 includes a coupler 206 for engagement with the face plate 250. After the partially segmented member 200 has been positioned, the guide member 220 can be removed during surgery prior to optional insertion of bone graft material in the space formed by the two vertebrae and the partially segmented member.

Figure 18:
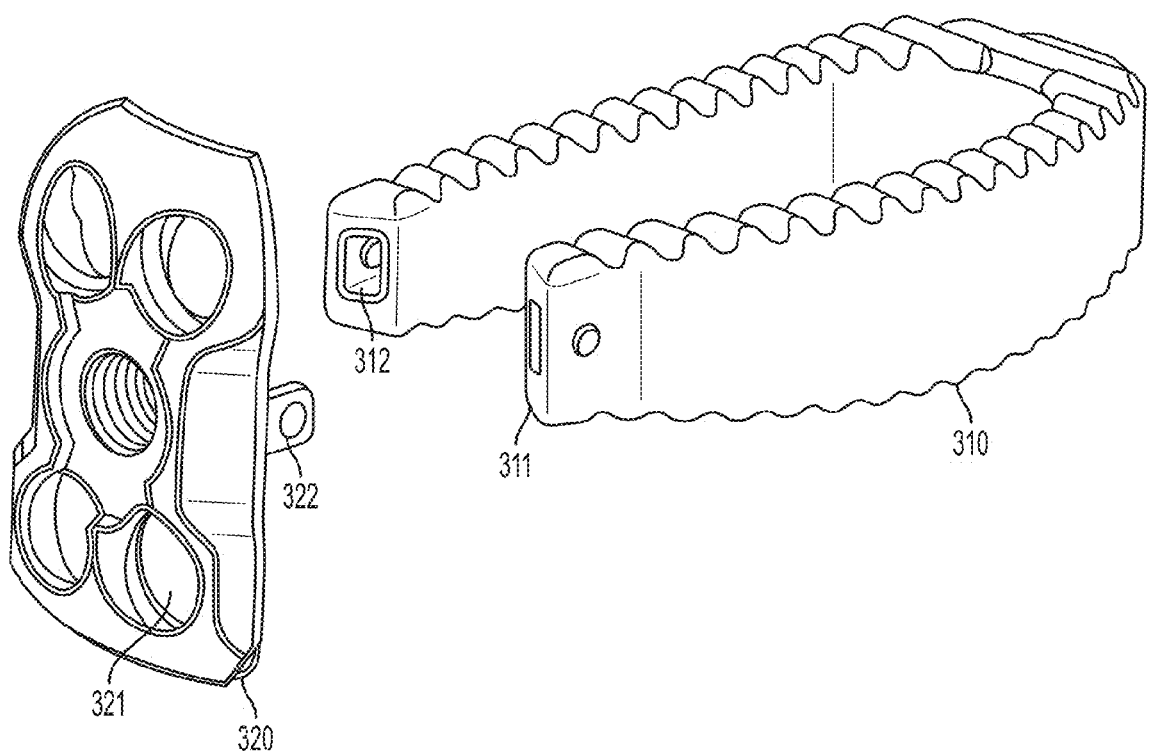
FIGS. 18-19 illustrate another embodiment of this invention, which employs a first component and a face plate, both sized and shaped for lateral implantation between vertebrae.
Figure 19:
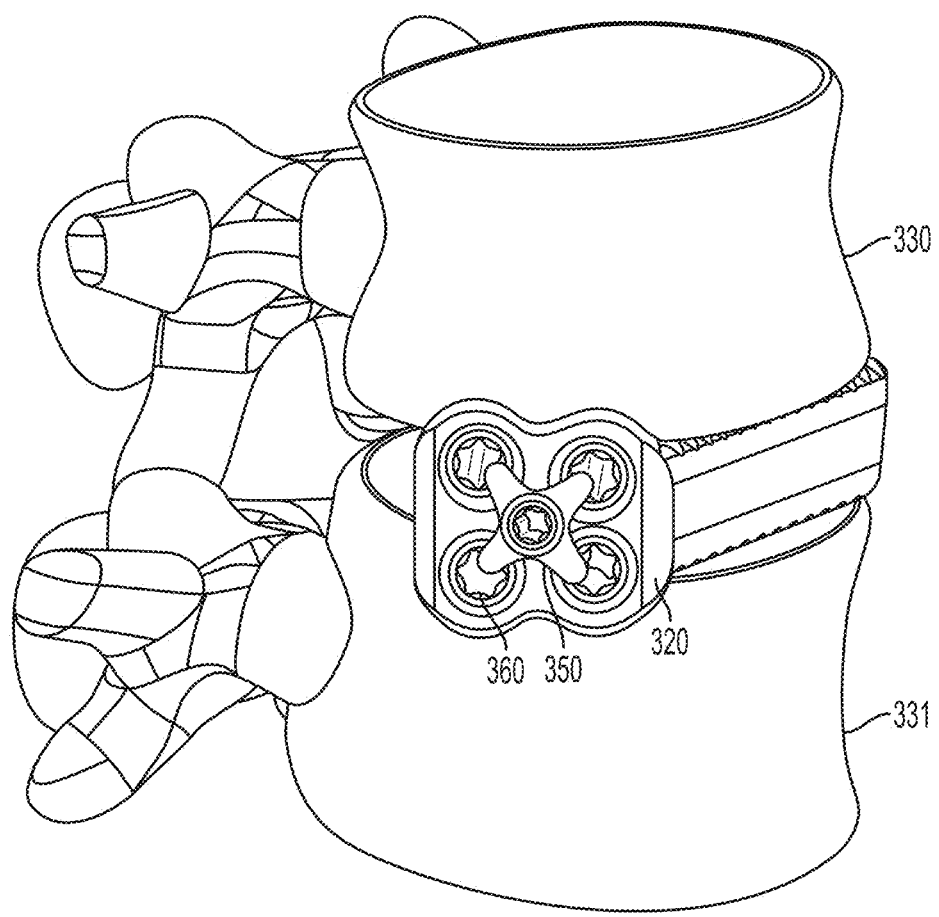
Figure 20:
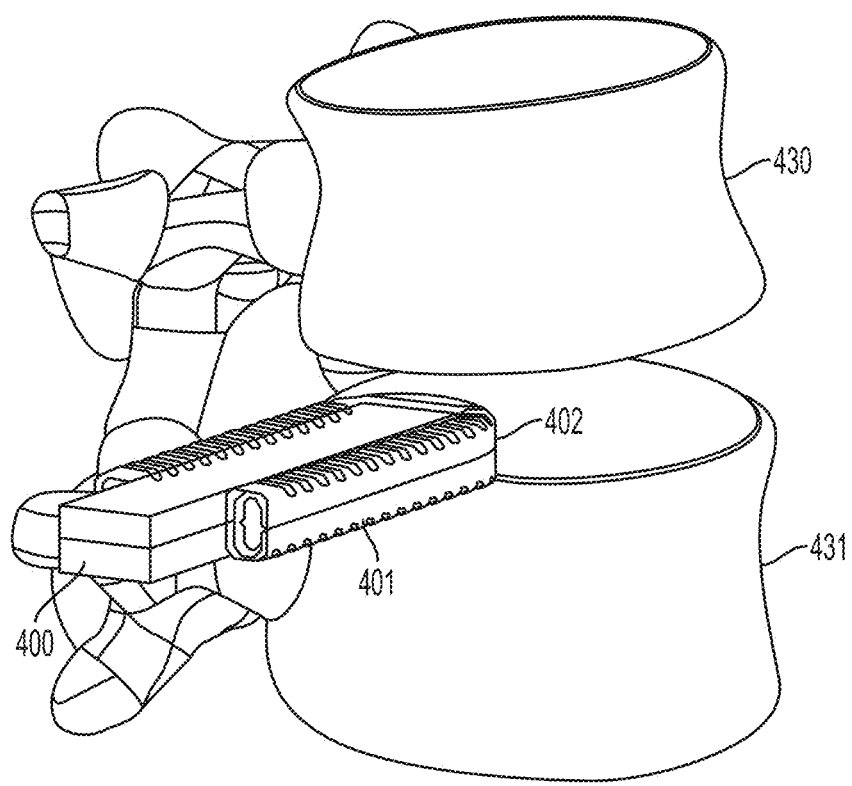
FIGS. 20-24 illustrate another embodiment of this invention, which uses upper and lower components inserted between vertebrae, then separated using spacers to form a generally U-shaped load bearing implant.

FIGS. 18 and 19 show another 2-piece embodiment of the invention. The implant includes a generally U-shaped first component 310 that includes couplers 311, 312 that are configured to mate with corresponding couplers 322 of the face plate 320. The face plate 320 includes two or more bores 321 for receiving fasteners. The bores are angled so that the fasteners contact the upper or lower vertebrae. FIG. 32 shows the device as implanted in a body, the first component 310 has been placed between the vertebrae 330, 331, bone graft packed in the void formed by the first component and the vertebrae, face plate 320 coupled to the first component 310, fasteners 360 screwed into the vertebrae, and fastener locking mechanism 350 engaged. The first component and face plate are configured and adapted such that their size and shape permit lateral implantation.

Figure 21:
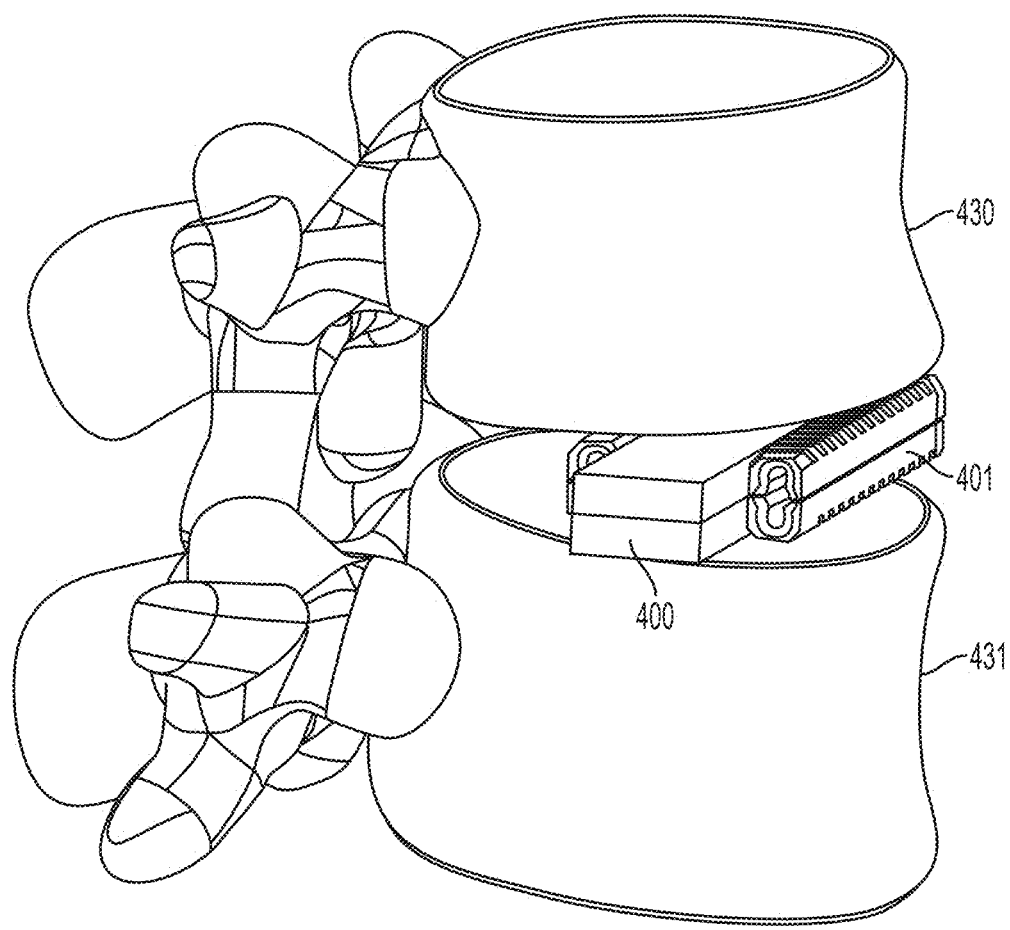
Figure 22:
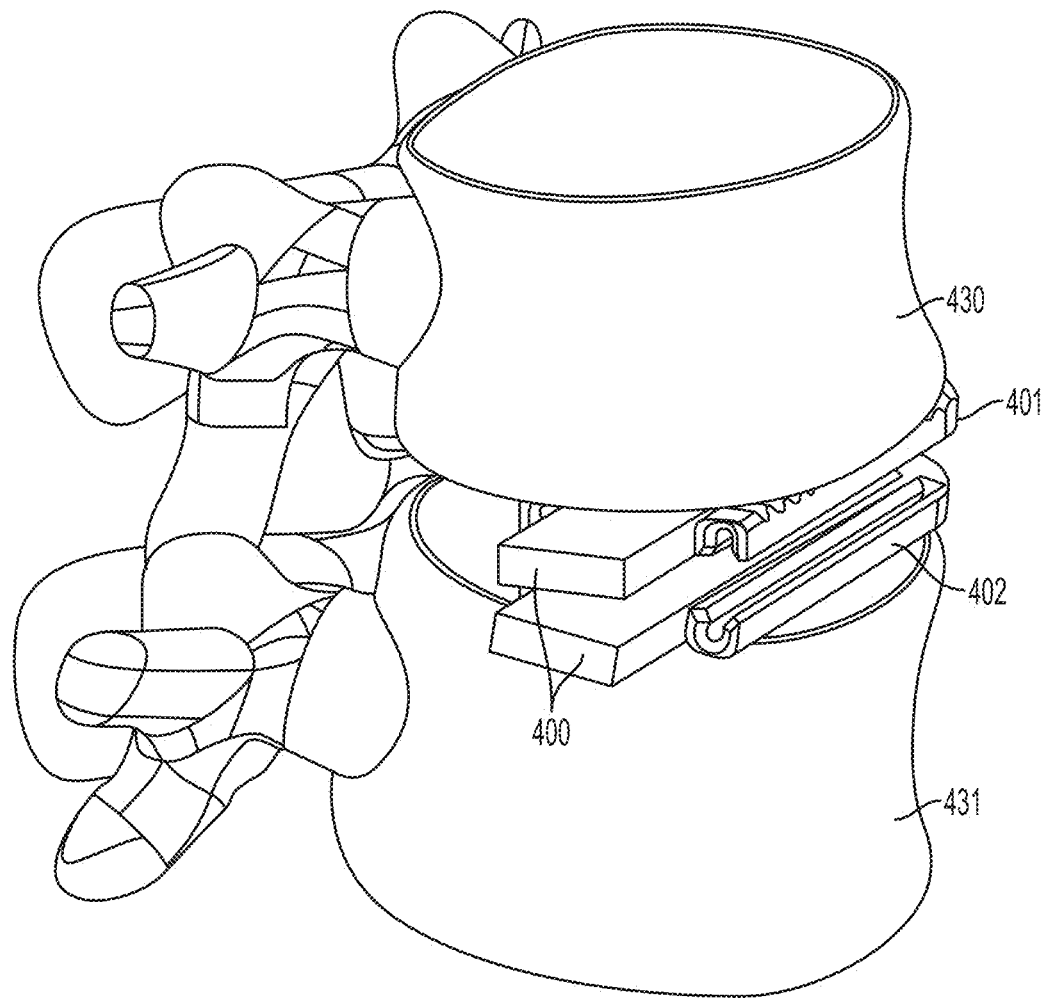
Figure 23:
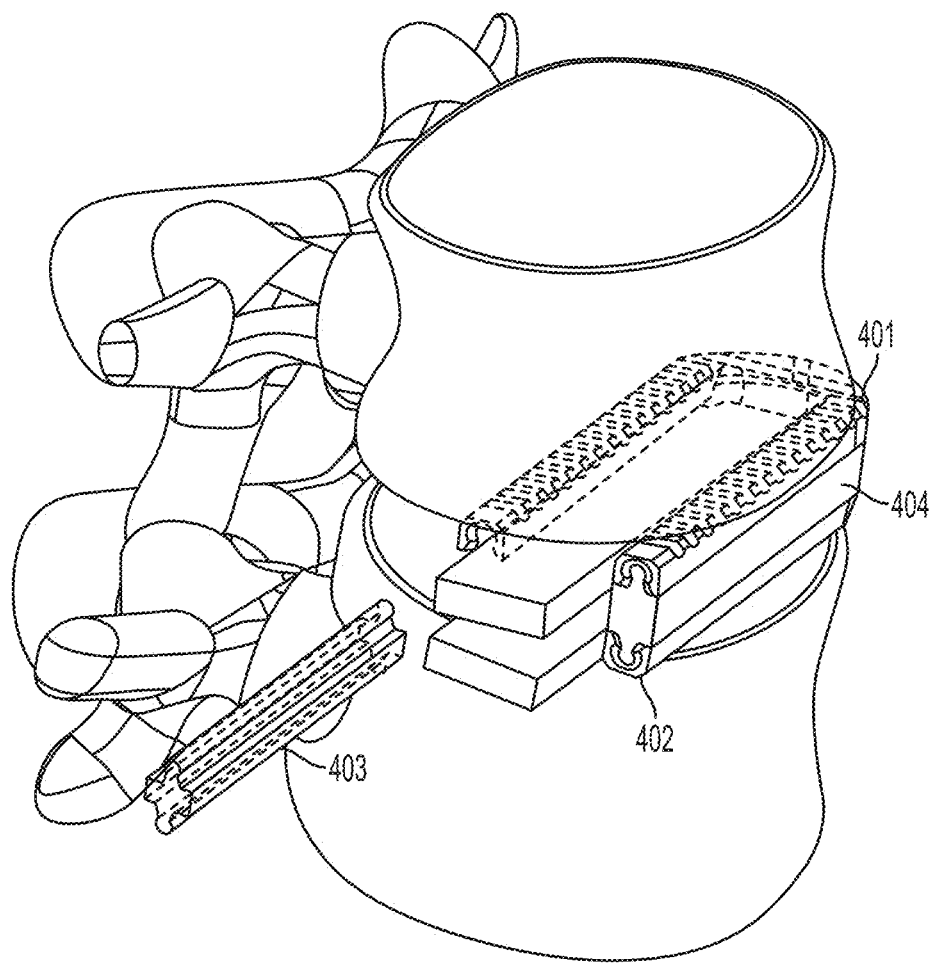
Figure 24:
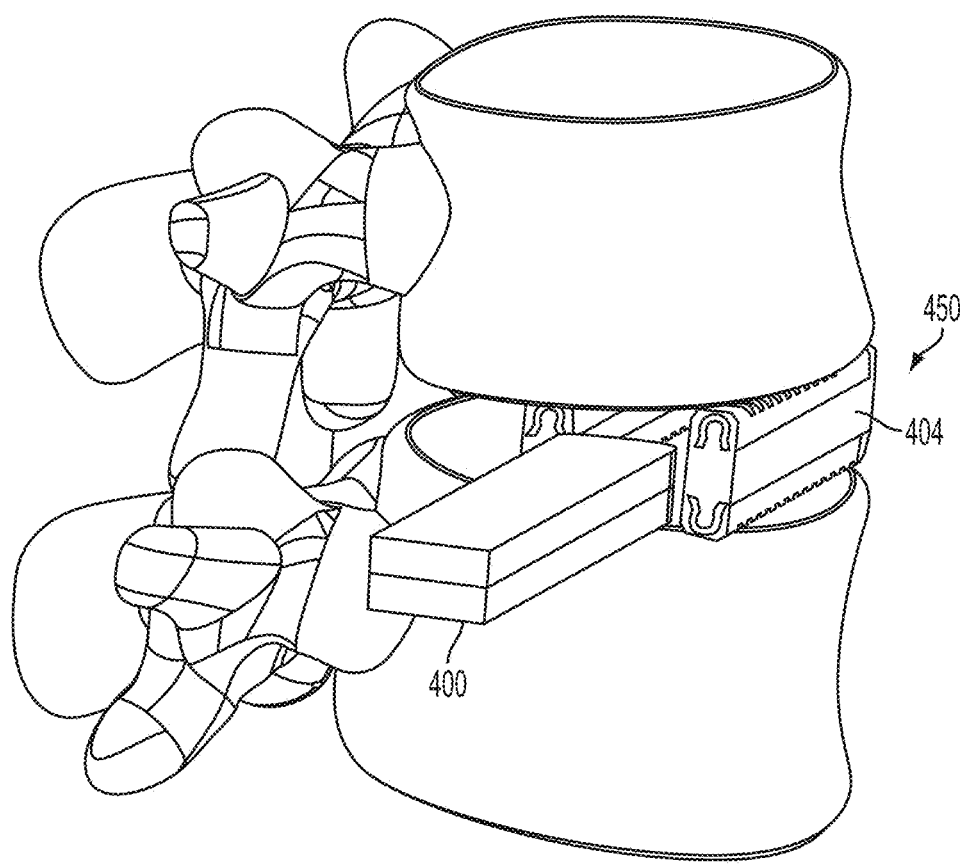

FIGS. 20-24 show another embodiment of this invention for lateral implantation. Upper and lower opposed components 401, 402 are placed between two vertebrae 430, 431, using a temporary spacing device 400 to optionally hold the upper and lower components 401, 402 together during placement. After being positioned, as shown in FIG. 21, the vertebrae are distracted as shown in FIG. 22, optionally using the temporary spacing device 400 to achieve proper distraction space. Next, front and back spacers 404, which are configured to fit into corresponding grooves in the upper and lower components 401, 402, are slid into place between the upper and lower components 401, 402, as shown in FIGS. 23 and 24 to thereby form the implant 350. Subsequently, the temporary spacing device 400 is removed. Next, bone graft material can be optionally placed in the void created by the implant 450 and two vertebrae. Lastly, a suitable face plate, configured to couple to corresponding couplers of the implant 450, can be coupled to the implant and fasteners screwed into the vertebrae to fix the implant in place.

For purposes of this disclosure, while the invention may be adaptable to various modifications and alternative forms, specific embodiments have been shown by way of example and described herein. However, it should be understood that the invention is not intended to be limited to the particular forms disclosed. Rather, the invention is to cover all modifications, equivalents, and alternatives falling within the spirit and scope of the invention as defined. Moreover, the different aspects of the disclosed methods and systems may be utilized in various combinations and/or independently. Thus the invention is not limited to only those combinations shown herein, but rather may include other combinations.

What is claimed is:

1. A spinal fusion device comprising:
    a load-bearing interbody component configured to fit between two adjacent vertebrae, wherein the interbody component comprises:
        an upper U-shaped component comprising:
            a first pair of members defining a space therebetween, each of the first pair of members comprising a first end and a second end, the first pair of members joined together at their second ends;
            a first groove formed into one member of the first pair of members and a second groove formed into the other member of the first pair of members;
        a lower U-shaped component comprising:
            a second pair of members defining a space therebetween, each of the second pair of members comprising a first end and a second end, the second pair of members joined together at their second ends;
            a first groove formed into one member of the second pair of members and a second groove formed into the other member of the second pair of members;
            wherein the first groove of the first pair of members and the first groove of the second pair of members are oriented toward one another when the spinal fusion device is in use;
    a first spacer comprising:
        a first tongue that extends an entire length of the first spacer;
        a second tongue that extends the entire length of the first spacer; and
        wherein the first tongue is adapted to slideably engage the first groove of the upper U-shaped component and the second tongue is adapted to slideably engage the first groove of the lower U-shaped component;
    a second spacer comprising:
        a first tongue that extends an entire length of the second spacer;
        a second tongue that extends the entire length of the second spacer; and
        wherein the second tongue is adapted to slideably engage the second groove of the upper U-shaped component and the second tongue is adapted to slideably engage the second groove of the lower U-shaped component; and
        wherein the upper U-shaped component and the lower U-shaped component are separate components that are not directly connected to each other.

2. The spinal fusion device of claim 1, further comprising a faceplate adapted to couple to the spinal fusion device and further adapted to couple to the two adjacent vertebrae to secure the spinal fusion device to the two adjacent vertebrae.

3. The spinal fusion device of claim 1, wherein:
    the first spacer defines a first width; and
    the second spacer defines a second width.

4. The spinal fusion device of claim 3, wherein the first width and the second width are different.

5. The spinal fusion device of claim 3, wherein the first width and the second width are the same.

* * * * *